United States Patent [19]

Sieverin

[11] Patent Number: 4,894,251
[45] Date of Patent: Jan. 16, 1990

[54] METHOD AND APPARATUS FOR INSPECTING CONTAINERS

[75] Inventor: Walter J. Sieverin, McHenry, Ill.

[73] Assignee: American National Can Company, Chicago, Ill.

[21] Appl. No.: 209,323

[22] Filed: Jun. 20, 1988

[51] Int. Cl.$^4$ .............................................. B05C 13/02
[52] U.S. Cl. .......................................... 427/8; 427/10; 118/503; 118/712; 118/713; 73/150 R; 324/71.1; 204/227; 204/434
[58] Field of Search ...................... 427/8, 10; 118/712, 118/713, 503; 73/150; 324/71.1; 204/227, 434

[56] References Cited

U.S. PATENT DOCUMENTS 3,417,327 12/1968 Breidenbach ........................ 73/150
3,869,910 3/1975 Scaletta ................................ 118/712
3,924,180 12/1975 Salzman .............................. 324/71.1

FOREIGN PATENT DOCUMENTS 260839 12/1985 Japan ................................. 324/71.1

OTHER PUBLICATIONS

Yoshitaka et al., "Electrochemical Degradation Measurement Method", English translation of Japanese Kokai Pat. No. 260839.

Primary Examiner—Shrive Beck
Assistant Examiner—Vi Duong Dang
Attorney, Agent, or Firm—Robert A. Stenzel; Ralph R. Rath

[57] ABSTRACT

A method of testing coating integrity of containers includes the steps of introducing a probe into an electrolytic solution into the container and applying a constantly-increasing voltage to the probe from a source and taking readings of the voltage when the current flow through the container reaches a predetermined level. The apparatus also includes a gripping mechanism for producing a positive contact between the metal in the container and the remainder of the circuit.

9 Claims, 2 Drawing Sheets

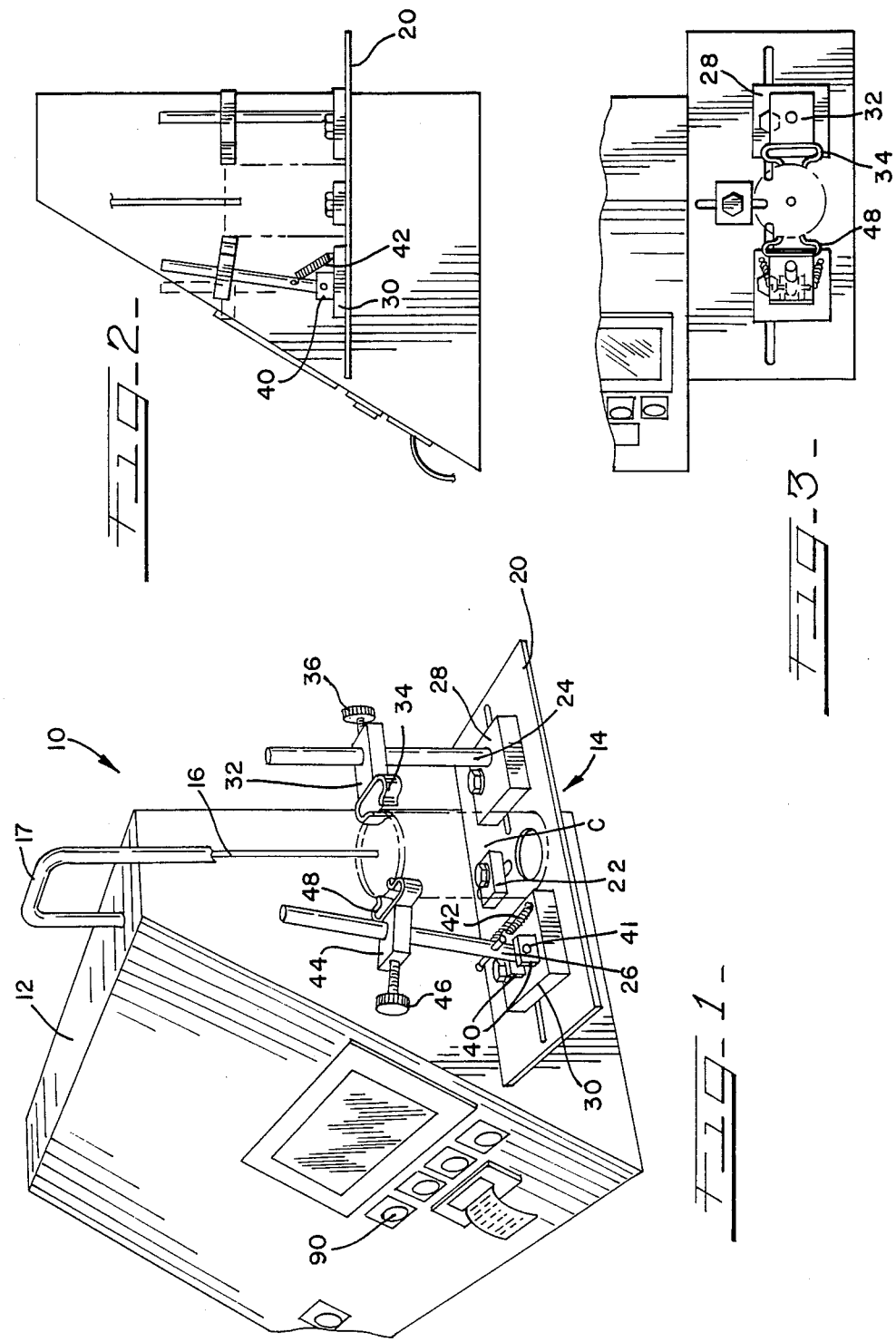

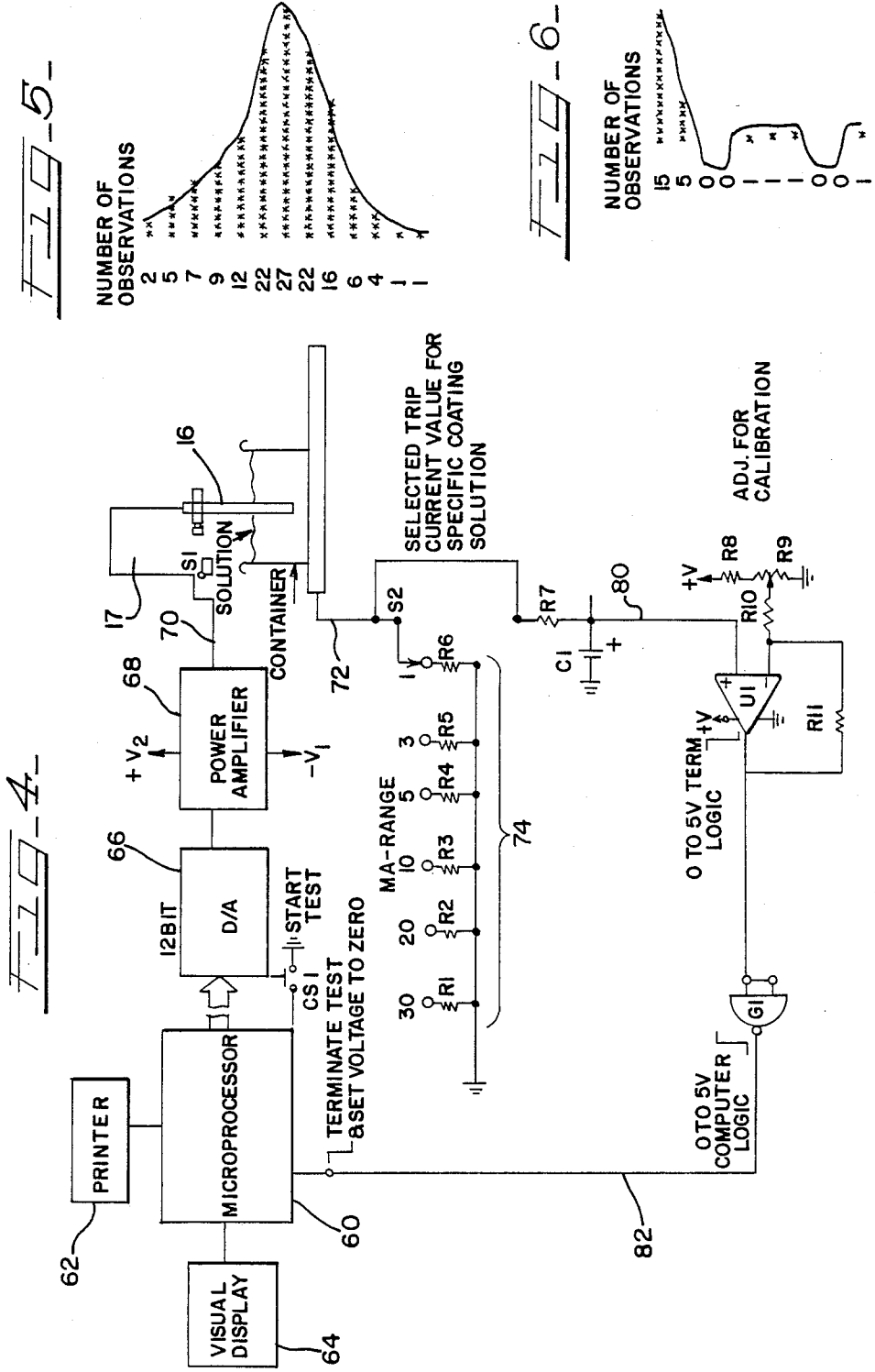

METHOD AND APPARATUS FOR INSPECTING CONTAINERS

TECHNICAL FIELD

The present invention relates generally to inspection apparatus for inspecting the quality of containers and, more particularly, to inspection apparatus for inspecting coating integrity on the inner surface of a metal container, such as welded, drawn or drawn and ironed type.

BACKGROUND PRIOR ART

Drawn and ironed metal containers have been in existence for a number of years and are utilized for packaging a variety of products. In the packaging of some of these products, it is necessary to provide a coating on the interior surface of the metal container to prevent the packaged product from picking up or absorbing some of the metal from the container wall and to protect the container from corrosive products. Normally, this coating is applied by introducing a spray nozzle through the open end of the container so that the container is coated along the bottom end wall, as well as the side wall. Because of the particular configuration of the end wall or bottom wall, it is sometimes difficult to obtain adequate or complete coating coverage on the bottom wall of the container.

Thus, it has been customary to do random testing for coating integrity prior to introducing the product into the container. It is well known to utilize an electrolytic solution along with a fixed voltage source and a probe placed into the solution to determine coating coverage integrity in coated containers. It is also well known that the type of solution, probe materials, polarity of test, the time duration of the test, and the voltage values are factors that determine the current value and, therefore, the coated container integrity.

One prior art-type of testing device that has been developed and is marketed by Waco (Wilkins-Anderson Co.), Chicago, Illinois. The testing device consists of a test fixture which supports and makes electrical contact with the container that has the electrolytic solution contained therein. A probe is introduced into the electrolytic solution and a fixed voltage source is applied to the probe and the current is recorded after a predetermined time period to ascertain coating integrity. In the prior art device, the probe is maintained "negative", while the container is maintained "positive", so that the conventional current flow is from the container through the solution to the probe.

Usually, the fixed voltage is approximately 6 volts in the prior art-type of testing device. The voltage was fixed and the current was the variable. A low current reading means that the coating integrity of the container is acceptable, while a high current reading means that the container is unacceptable.

SUMMARY OF THE INVENTION

According to the present invention, a more sensitive and significantly improved method for testing coated metal containers has been developed which relies upon a variable voltage concept rather than a fixed voltage concept. This concept tests all containers to the same current point.

More specifically, according to the method aspect of the invention, a container is placed into a test station and an electrolytic solution is poured into the container. A desired current range for the particular container is selected utilizing a variable resistance switching system. Then a positive increasing voltage ramp of some specific volts/sec is applied to the probe and a comparator is tripped when the conducting current reaches the selected current value. A microprocessor then displays and records the voltage reading at which the comparator is tripped.

One of the significant advantages of the present invention is that the data obtained follows a normal distribution curve and statistical analysis equations apply. In contrast, in the prior art inspection apparatus, the probe is "negative", the container is "positive", resulting in an exponential curve and statistical analysis is difficult since the curve would have to be mathematically reformed to a normal distribution curve. It is well known in the prior art that a negative probe and positive container plates out the container sites and causes much lower readings than if the prob was positive and the container was negative.

According to a further aspect of the invention, the apparatus includes novel means for grounding the container. More specifically, the inspection apparatus includes a fixture that has a base for supporting the container and gripping means extending above the base for engaging an upper edge of the container. The gripping means preferably includes first and second posts that extend above the base and each have resilient contact elements on an upper edge thereof for engaging an exposed edge of said container. In its more preferred form, one of the posts is pivoted on the base and is spring-biased towards the other post so that the resilient contacts are biased towards each other and into engagement with the peripheral exposed edge of the container so that the container edge is gripped between the two resilient contacts.

BRIEF DESCRIPTION OF DRAWINGS

FIG. 1 is a perspective view of the testing apparatus of the present invention;

FIG. 2 is a side elevational view of the test fixture;

FIG. 3 is a plan view of the test fixture;

FIG. 4 is a schematic diagram of the control circuit;

FIG. 5 is a histogram of data from a series of tests conducted on one type of container; and, FIG. 6 is a histogram of the prior art data.

DETAILED DESCRIPTION

While this invention is susceptible of embodiment in many different forms, there is shown in the drawings and will herein be described in detail a preferred embodiment of the invention with the understanding that the present disclosure is to be considered as an exemplification of the principles of the invention and is not intended to limit the broad aspect of the invention to embodiment illustrated.

FIG. 1 of the drawings discloses a test apparatus 10 including a control panel 12 and a test fixture 14. The control panel 12 includes a probe 16 supported on a support 17 and is adapted to be inserted into a container C and is electrically connected to a circuit, to be described in detail hereinafter. The support 17 is slidably supported on control panel 12.

The test fixture 14 includes a base 20 that defines a support for the container C and has an adjustable stop 22 located thereon which defines an abutment for positioning the periphery of the container with respect to the probe so that the probe is located in the center of the container during the testing operation.

The test fixture 14 also includes a pair of posts 24 and 26 which have lower support pedestals 28 and 30 horizontally adjustably supported on base 20. The post 24 is affixed to the pedestal 28 and has an adjustable bracket 32 supported thereon. The adjustable bracket 32 supports a resilient ground-engaging contact 34 which is generally C-shaped in plan view, as shown in FIG. 3. The bracket 32 is retained in a vertically-adjustable position through a hand knob screw 36.

The second post 26 is preferably pivotally supported on pedestal 30 through a pivot pin 41 extending between brackets 40 and is pivotally biased by a pair of springs 42 extending between the post 26 and the pedestal 30. An adjustable bracket 44 is retained in an adjusted position by a hand knob screw 46 and has a resilient ground contact 48 supported thereon. All of the elements that form part of fixture 14 are formed from a conductive metal material and the entire fixture is connected by a ground lead 72 (FIG. 4) to a ground located internally of the control panel 12, for a purpose to be described later.

As is well known, in the formation of metal drawn and ironed containers C, it is customary to draw and iron a metal, such as aluminum, steel or tinplate, to a general configuration and desired height, after which the upper edge is trimmed to a predetermined height and an outwardly-directly flange is then formed around the upper open end, which is utilized for seaming an end to the container after the product has been inserted. Thus, the peripheral edge of the outwardly-directed flange is exposed metal without any coating or labeling thereon, which is customarily found on the internal surface of the container, as well as the external surface. With the construction of the test fixture 14 described above, a good contact is made between the resilient clamps 34 and 48 and the peripheral edge of the flange of the container. This type of ground connection is superior to what has heretofore been utilized in test fixtures of this type.

FIG. 4 discloses the components and circuitry incorporated into the control panel 12 for producing a voltage ramp to the probe 16 and taking a reading of the voltage when the current flow reaches a predetermined level or intensity. Thus, the control circuit includes a microprocessor 60 having a printer 62 and a visual display 64 associated therewith.

The microprocessor 60 has an output connected to a 12-bit digital-to-analog converter 66, which in turn is connected to a power amplifier 68 which has its output lead 70 connected to the probe 16. A switch S1 is associated with the support mechanism 17 for the probe and switch S1 is closed when the probe is in a proper position within the electrolytic solution in the container C. The closure of switch S1 closes normally-open contacts CS1 to initiate the start of a test within the microprocessor 60, as will be explained later.

The container ground lead 72 is connected to a second switch S2 which in turn is connected through a selectable resistor means 74 to ground. The selectable resistor means includes a plurality of parallel fixed resistors, respectively indicated by R1 through R6, for selecting the current range for a particular container, as will be described later.

A branch lead 80 having resistor R7 in series therewith and a capacitor is connected to the positive terminal of a comparator U1. The negative terminal of comparator U1 has a positive voltage applied thereto from a source through a fixed resistor R8 and adjustable resistor R9 used for calibration purposes and a fixed resistor R10.

Thus, a preset voltage can be set at the negative input terminal of the comparator U1 and the output of the comparator will be low so long as the voltage corresponding to the current flow through the variable resistor means 74 is below the preset voltage. The output of the comparator U1 is, in turn, connected to an invertor G1 which produces a high output when the output from the comparator is low and produces a low output when the output from the comparator is high. The output of the invertor G1 is, in turn, connected to the microprocessor through lead 82.

In the operation of the system so far described, the initial setting of the desired range of current flow is selected by positioning switch S2 to form a connection between any one of the selected variable resistors R1 through R6, which will be dependent upon the type of solution that is being utilized, the container that is being tested, and the coating that has been applied to the internal surface of the container.

After the selection is made through the operation of any one of at least four control knobs 90 located on control panel 12, the probe is introduced into the electrolytic solution and the probe actuates switch S1 when the probe is in the proper position, centered within the container and a predetermined distance above the bottom thereof. This initiates the test, which causes the microprocessor to produce an increasing voltage to the digital-to-analog converter, which is then amplified and passes through the probe 16 into the electrolytic solution. The electrolytic solution thus acts as a conductor for conducting current flow to line 72 and switch S2 to ground.

When the current flow through the container reaches the predetermined range, the corresponding output voltage will be transmitted through lead 80 to comparator U1 and cause the comparator output to go high, which in turn will cause the invertor to go low, and will produce a signal to the microprocessor 60 to terminate the test and print and visually display the voltage at that point.

Thus, the testing apparatus of the invention provides a much more sensitive and more accurate result than has heretofore been possible. Furthermore, the results are subject to accurate statistical analysis. For example, FIG. 5 shows the statistical analysis of a test run for a number of different containers and shows the typical histogram developed therefrom. FIG. 6 is a comparison of the histogram of the prior art-type fixed voltage testing devices and it can readily be seen that the curve is much more unpredictable since the majority of the readings are below the 1 milliamp current rating.

The values of the respective resistors is as follows:

R1 = 10
R2 = 15
R3 = 30
R4 = 60
R5 = 100
R6 = 300
R7 = 10K
R8 = 16K
R9 = 500
R10 = 10K
R11 = 2.2M

While the specific embodiments have been illustrated and described, numerous modifications come to mind without significantly departing from the spirit of the invention and the scope of protection is only limited by the scope of the accompanying claims.

What is claimed is:

1. A method of detecting the integrity of a coating on an inner surface of a container having an outwardly-directed flange surrounding an open end thereof with said flange having an uncoated peripheral edge comprising the steps of introducing an electrolytic solution into said container, producing a ground connection with said peripheral edge of said container, introducing a probe into the solution in said container, producing a voltage of increasing intensity to said probe, and taking a reading of said voltage when the current flow reaches a predetermined intensity.

2. A method as defined in claim 1, in which said probe has a positive D.C. voltage applied thereto.

3. A method as defined in claim 2, in which said voltage is applied at a constantly-increasing intensity.

4. A method as defined in claim 1, in which said ground connection includes opposed contact members that are biased toward each other to grip the container therebetween.

5. Inspection apparatus for inspecting coating integrity in a container comprising a fixture including a base for supporting said container with gripping means extending above said base for engaging an upper edge of said container and grounding said container, and a probe insertable into an electrolytic solution in said container.

6. Inspection apparatus as defined in claim 5, in which said gripping means includes first and second posts extending above said base, each having resilient contact elements on an upper edge thereof for engaging an exposed surface of said container.

7. Inspection apparatus as defined in claim 6, in which one of said posts is fixed to said base and the other of said posts is adjustable with biasing means for biasing said contacts toward each other.

8. A method of detecting the integrity of a coating on an inner surface of a metal container comprising the steps of introducing an electrolytic solution into said container, producing a ground connection to said container, introducing a probe into the solution in said container, introducing a predetermined resistance between said container and said ground connection, producing a voltage of increasing intensity to said probe to produce current flow between said container and said ground connection, and taking a reading of said voltage when the current flow from said container reaches a predetermined intensity.

9. A method as defined in claim 8, in which said resistance is variable.

* * * * *